United States Patent
Beck et al.

(10) Patent No.: US 9,675,332 B2
(45) Date of Patent: Jun. 13, 2017

(54) SURGICAL RETRACTOR

(71) Applicant: Aesculap AG, Tuttlingen (DE)

(72) Inventors: Thomas Beck, Durchhausen (DE);
Peter Kleine, Neu Isenburg (DE);
Dieter Weisshaupt, Immendingen (DE);
Pedro Morales, Tuttlingen (DE);
Robert Vogtherr, Tuttlingen (DE);
Andreas Elisch, Schramberg (DE)

(73) Assignee: Aesculap AG, Tuttlingen (DE)

( * ) Notice: Subject to any disclaimer, the term of this patent is extended or adjusted under 35 U.S.C. 154(b) by 357 days.

(21) Appl. No.: 14/327,807

(22) Filed: Jul. 10, 2014

(65) Prior Publication Data

US 2015/0018624 A1    Jan. 15, 2015

Related U.S. Application Data

(63) Continuation of application No. PCT/EP2012/074802, filed on Dec. 7, 2012.

(30) Foreign Application Priority Data

Jan. 13, 2012 (DE) .................. 10 2012 100 284

(51) Int. Cl.
*A61B 17/02* (2006.01)
*A61B 1/32* (2006.01)

(52) U.S. Cl.
CPC .......... *A61B 17/0206* (2013.01); *A61B 1/32* (2013.01)

(58) Field of Classification Search
CPC .............................. A61B 17/0206; A61B 1/32
See application file for complete search history.

(56) References Cited

U.S. PATENT DOCUMENTS

| 979,305 A | 12/1910 | Hunt |
| 2,670,731 A | 3/1954 | Zoll et al. |

(Continued)

FOREIGN PATENT DOCUMENTS

| DE | 1 769 072 | 6/1958 |
| DE | 2 359 085 | 6/1974 |

(Continued)

OTHER PUBLICATIONS

"Fiberoptics for Surgery", Applied Fiberoptics, Inc., cover page, pp. 5, 6, and two product information sheets, undated. (retyped p. 6 attached for clarity).

(Continued)

*Primary Examiner* — Ellen C Hammond
(74) *Attorney, Agent, or Firm* — Lipsitz & McAllister, LLC (57) ABSTRACT

The invention relates to a surgical retractor, particularly for the retraction of a separated sternum, with a holding device and two spreader arms, wherein the spreader arms are mounted with one end on the holding device, at a distance from each other that is adjustable in a spreading plane, and at least two retaining elements for retention of bone material, for example of the separated sternum, are arranged on each of the spreader arms. To develop this retractor for sternotomy in such a way as to permit gentler opening of the separated sternum, it is proposed that at least one of the retaining elements is mounted such that its position can be modified in the retraction direction with respect to that end of the spreader arm mounted on the holding device.

24 Claims, 10 Drawing Sheets (56) References Cited

U.S. PATENT DOCUMENTS

| | | |
|---|---|---|
| 3,195,536 A | 7/1965 | Hovnanian et al. |
| 3,522,799 A | 8/1970 | Gauthier |
| 3,592,199 A | 7/1971 | Ostensen |
| 3,749,088 A | 7/1973 | Kohlmann |
| 3,796,214 A | 3/1974 | Davis |
| 3,986,854 A | 10/1976 | Scrivo et al. |
| 4,562,832 A | 1/1986 | Wilder et al. |
| 4,566,448 A | 1/1986 | Rohr, Jr. |
| 4,570,614 A | 2/1986 | Bauman |
| 4,597,030 A | 6/1986 | Brody et al. |
| 4,747,394 A * | 5/1988 | Watanabe .......... A61B 17/0206 600/217 |
| 4,805,599 A | 2/1989 | Ray |
| 4,867,139 A | 9/1989 | Girzadas |
| 4,932,395 A | 6/1990 | Mehdizadeh |
| 4,971,038 A | 11/1990 | Farley |
| 5,002,547 A | 3/1991 | Poggie et al. |
| 5,027,793 A | 7/1991 | Engelhardt et al. |
| 5,035,232 A | 7/1991 | Lutze et al. |
| 5,303,694 A | 4/1994 | Mikhail |
| 5,363,841 A | 11/1994 | Coker |
| 5,364,399 A | 11/1994 | Lowery et al. |
| 5,618,260 A * | 4/1997 | Caspar ............... A61B 17/0206 600/201 |
| 5,728,046 A * | 3/1998 | Mayer ............... A61B 17/0293 600/210 |
| 5,730,757 A | 3/1998 | Benetti et al. |
| 5,944,736 A | 8/1999 | Taylor et al. |
| 5,976,171 A | 11/1999 | Taylor |
| 6,113,536 A | 9/2000 | Aboul-Hosn et al. |
| 6,478,734 B1 | 11/2002 | Taylor et al. |
| 6,602,189 B1 | 8/2003 | Bennetti et al. |
| 7,288,065 B1 | 10/2007 | Taylor et al. |
| 7,699,774 B1 | 4/2010 | Taylor et al. |
| 7,909,846 B1 | 3/2011 | Taylor et al. |
| 8,092,495 B2 | 1/2012 | Boulis et al. |
| 8,715,175 B2 | 5/2014 | Assaker et al. |
| 2003/0060686 A1 | 3/2003 | Taylor et al. |
| 2007/0161865 A1 | 7/2007 | Fakhrai |
| 2008/0139879 A1 | 6/2008 | Olson et al. |
| 2008/0183046 A1 | 7/2008 | Boucher et al. |
| 2008/0188718 A1 | 8/2008 | Spitler et al. |
| 2009/0203969 A1 | 8/2009 | Cohen et al. |
| 2009/0259107 A1 | 10/2009 | Crenshaw et al. |
| 2010/0030184 A1 | 2/2010 | Boulis et al. |
| 2010/0185059 A1 | 7/2010 | Sperling et al. |
| 2012/0022335 A1 | 1/2012 | Assaker et al. |
| 2013/0046147 A1 | 2/2013 | Nichter et al. |

FOREIGN PATENT DOCUMENTS

| | | |
|---|---|---|
| DE | 30 23 266 | 1/1982 |
| DE | 33 01 890 | 7/1984 |
| DE | 297 23 643 | 1/1999 |
| DE | 20 2011 051 999 | 1/2012 |
| EP | 0 101 781 | 3/1984 |
| EP | 0 101 871 | 3/1984 |
| EP | 0 327 249 | 8/1989 |
| EP | 0856286 | 8/1998 |
| EP | 2 394 584 | 12/2011 |
| FR | 2 692 468 | 12/1993 |
| FR | 2742330 | 6/1997 |
| JP | S12-4341 | 4/1937 |
| WO | WO 01/80725 | 11/2001 |
| WO | 2009/124244 | 10/2009 |

OTHER PUBLICATIONS

Aurelio Chaux, M.D., and Carlos Blanche, M. D., "A New Concept in Sternal Retraction: Applications for Internal Mammary Artery Dissection and Valve Replacement Surgery". The Annals of Thoracic Surgery, vol. 42, No. 4, Oct. 1986, pp. 473-474.

* cited by examiner

SURGICAL RETRACTOR

This application is a continuation of International application No. PCT/EP2012/074802 filed on Dec. 7, 2012 and claims the benefit of German application no. 10 2012 100 284.3 filed on Jan. 13, 2012, which are incorporated herein by reference in their entirety and for all purposes.

BACKGROUND OF THE INVENTION

The invention relates to a surgical retractor, particularly for the spreading of a parted sternum, with a holding device and two spreader arms, said spreader arms being held with one end on the holding device at a spacing from one another that is adjustable in a spreading plane. One or more retaining elements are arranged on each of the spreader arms for the retention of bone material, for example the parted sternum.

Surgical retractors of the aforementioned type are used, in particular, for operations on the heart in order to gain suitable access. The sternum is parted centrally in the longitudinal direction thereof and the sternum halves are forced back to either side, i.e. retracted, together with the adjacent ribs, by means of the retractor.

As a result of the shape and arrangement of the ribs, the observed stiffness at the cranial end of the sternum halves is significantly greater than at the caudal end.

As a result of the varying stiffness, with conventional retractors in particular, in which the achieved opening widths of the sternum are the same in the cranial and caudal directions, in the absence of any additional setting or adjusting capability, unfavourable forces arise along the vertical axis of the sternum.

Particularly in the case of the cranially positioned ribs, due to the substantially greater stiffness there, larger forces occur than at the caudally positioned ribs. This, in turn, results in increased stresses in these ribs, as a result of which greater postoperative pain can occur.

The pain results, above all, if a cranially positioned rib damages the brachial plexus (Plexus brachialis) which is positioned in the region of the shoulder, due to the deformation of said rib or even splintering of pieces off the rib in this region.

In an extreme case, the breakage of a cranially positioned rib can even occur. Since these ribs are positioned under the clavicle, rib breakages are not detected in a normal X-ray image. However, recent studies show that they occur more often than previously suspected.

From US 2007/0161865 A1, there is known a surgical retractor in which this problem is partially taken into account in that the holding device is configured slightly bow-shaped so that the retaining elements arranged at the free ends of the spreader arms perform a slightly bow-shaped movement during retraction. A further adaptation is enabled by a spreader arm which is held on the holding device pivotable in the spreading plane. However, the latter requires additional intervention and adjustment, making the process more complex and more time-consuming.

It is an object of the present invention further to develop the retractor mentioned in the introduction for sternotomy such that a gentler opening of the parted sternum is made possible.

SUMMARY OF THE INVENTION

The object of the present invention is achieved with a surgical retractor having the features set forth in the claims and discussed in detail below.

Due to the mounting of at least one of the retaining elements being positionally changeable in the retraction direction relative to a spreader arm, it is possible, when the sternum is opened by the retractor, to change and adapt within a certain range the forces which act on the cranially and caudally positioned rib arches. This is achieved in many of the embodiments of the invention without the surgeon having to intervene or make adjustments for this purpose.

In this way, the ribs adjacent to the sternum are more evenly loaded so that the danger of stress peaks in individual ribs which, in the worst case, can lead to fractures, can be significantly reduced.

If a pair of retaining elements mounted to be positionally adjustable is provided, they can be held on a common spreader arm or preferably in opposing positions, each on one of the spreader arms, for example, each adjacent to the end of the spreader arms held on the holding device.

It is most preferable if all the retaining elements are held so as to be positionally adjustable on the spreader arms.

For the positionally adjustable mounting, there are several preferred possibilities, which will be discussed subsequently. If a plurality of the retaining elements of a rectractor according to the invention are mounted to be positionally adjustable, they can be held in different ways on the spreader arms according to the different possibilities, as discussed below.

According to a first preferred embodiment of the invention, the at least one retaining element is mounted in its position in the retraction direction resiliently relative to the spreader arm. By means of the resilient mounting, the adaptation of the forces acting on the parted sternum is achieved with a noticeable effect even when using single-piece, rigid spreader arms.

More preferably, a pair of the retaining elements is resiliently mounted on the spreader arm(s) and most preferably, all the retaining elements are mounted resiliently in the retraction direction on the spreader arms.

In a second preferred embodiment according to the invention, at least one of the spreader arms of the surgical retractor is divided into two sections wherein a first section of the spreader arm is held substantially rigidly on the holding device and a second section of said spreader arm is held on the first section rotatable about an axis perpendicular to the spreading plane. The positional change is achieved here by means of pivoting of the second part of the spreader arm during the retraction process, again without any manual intervention by the surgeon.

Preferably, in this embodiment, the second section is resiliently held in a starting position substantially colinear or coaxial with the first section. As force acts parallel to the spreading plane during the retraction, the second section is pivoted against the first section, against the resilience.

More preferably, the pivoting movement is limited to a predetermined angle by means of a stop.

Preferably, in this embodiment of the retractor according to the invention, both spreader arms are subdivided into two sections wherein a first section of each spreader arm is held substantially rigidly on the holding device and the second section of the spreader arms is held on the first section rotatable about a pivot axis perpendicular to the spreading plane.

Preferably, in this embodiment, a first retaining element is held on the first section of the spreader arm which is rigidly connected to the holding device and a second retaining element is held on the second, pivotable section of the spreader arm.

In a variant of this embodiment, it can be provided that the second section can be locked, if needed, in a position pivoted relative to the first section.

In a further variant of this embodiment, it is provided that the second section is pivotable relative to the first section by means of a drive, wherein the drive is preferably configured to be self-locking.

Preferably, in the second embodiment of the retractor according to the invention, the first section of the spreader arm(s) has a length which is greater than half the overall longitudinal extent of the spreader arm.

In a third embodiment of the retractor according to the invention, two retaining elements are arranged on the second section, wherein the pivot axis which connects the first section to the second section is arranged between the retaining elements. Preferably, approximately half of the second section overlaps, in the longitudinal extent thereof, with the longitudinal extent of the first section of the spreader arm. There is then preferably no retaining element arranged on the first section of the spreader arm.

In the second and third embodiment, according to one variant, the first section of the spreader arm is formed substantially straight. In a further variant, the free end of the first section, on which the second section is pivotably mounted, is formed angled, the angled region projecting in the spreading plane toward the respective other spreader arm. The second section is then mounted on the free end of the angled part, pivotable in the spreading plane.

Here also there are several variants for the mounting of the second section on the first section of the spreader arm.

According to a first variant, the second section of the spreader arm is resiliently held in a starting position with a preferably parallel orientation relative to the first section.

According to a second variant, the second section is lockable on the first section in a pre-defined pivot position.

According to a third variant, the pivotability of the second section relative to the first section is limited by a stop.

According to a fourth variant, the second section is mounted pivotable relative to the first section by means of a drive, wherein the drive is preferably configured to be self-locking.

In general, it is preferred in the second and third embodiments if the retaining elements are arranged at a substantially equal spacing from the pivot axis of the second section of the spreader arm. The pivot axis is preferably arranged substantially centrally to the longitudinal direction of the second section.

Furthermore, the pivot axis of the second section can be fixable at a plurality of positions along the longitudinal direction of the second section. Preferably, the second section has a plurality of mounting bushings for this purpose.

In another alternative, it is provided that the pivot axis is formed by a bearing element which is displaceably held on the first section.

According to a fourth embodiment of the invention, the second section is held at a flexibly elastic region of the first section.

If the first section of a spreader arm is configured to be angled at the free end thereof, in one variant, the angled region can be divided to be fork shaped in the spreading plane. Then the second section is preferably subdivided into two separate longitudinal elements of which each is connected to one of the fork prongs.

The second spreader arm itself also can be configured flexibly elastic in the spreading plane and can thus further lead to or contribute to the positionally changeable holding of the retaining elements.

The invention also relates to a surgical retractor of the type mentioned in the introduction, wherein the two spreader arms are subdivided into two segments seen in the longitudinal direction, wherein a first segment is held with one end on the holding device in a substantially unchangeable orientation relative to the spreading plane and wherein a second segment is held at the free end of the first segment, so as to be pivotable about a pivot axis in a plane perpendicular to the spreading plane. Typically, the pivot axis extends transversely to the longitudinal direction of the spreader arms.

Preferably, the pivotal angle of the second segment is restricted by means of a stop so that preferably a pivot movement of the second segment is possible only in a direction out of the spreading plane.

According to a further preferred aspect, the length of the first segment is smaller than that of the second segment and is preferably approximately 30% or less of the overall length of the spreader arm.

More preferably, the retaining elements are directly or indirectly held exclusively on the second segment of the spreader arms.

The subdivision of the spreader arms into two segments wherein the second segment is pivotably held on the first segment has the advantage that the geometry of the surgical retractor can adapt to the shape of the torso of the patient, so that the space required by the device and thus at the same time any possible hindering of the surgeon can be lessened.

Insofar as the spreader arms are subdivided into a first and a second section, the joint connection between the first and the second segment is preferably arranged in the first section.

It should be noted at this point that the subdivision of the spreader arms, firstly, into a first and a second section and, secondly, into a first and a second segment do not represent competing concepts, but rather two concepts which can be simultaneously realised in one embodiment of a surgical retractor according to the invention.

In all the previously described embodiments and all the variants thereof, in additional to the positional adjustability possibly provided there, the retaining elements can be resiliently held on the spreader arms or the first and/or second sections thereof. The resilient mounting can be used herein for further improvement of the adaptation of the forces acting on the parted sternum.

For all the above described embodiments, it is the case that the retaining elements are preferably adjustable in the spacing thereof along the spreader arm. This enables a further optimisation of the retractor according to the invention with regard to the introduction of the forces onto the bone material lying against the retaining elements.

In order to achieve the most favourable possible geometry for introducing the retractor into the gap of the parted sternum, the retaining elements of the two spreader arms are arranged offset relative to one another in the longitudinal direction thereof. Thus the spreader arms can initially be brought into maximum proximity to one another.

Further preferred retaining elements which can be used in the retractors according to the invention are formed in two parts.

Preferably in this regard, a first part of the retaining element is held as a bearing part on the spreader arm and the second part, which is formed as a retaining surface, is mounted on the first part to be movable, in particular pivotable about an axis oriented perpendicular and/or parallel to the spreading plane.

Preferred retaining elements have a retaining surface with a maximum extent parallel to the longitudinal direction of the spreader arm in a region with which the bone material typically comes into contact, whilst the extent thereof adjacent, on the one hand, to the spreader arm and/or, on the other hand, at the free end of the retaining surface is selected to be smaller. This provides the surgeon with a better view, for example, during preparation of an Arteria mammaria.

Particularly advantageous is a web-like narrowly constructed free end of the retaining surface which can also be configured bent over so that the bone material of the sternum is securely gripped.

Preferred retaining elements have a bearing part in which a locking device is integrated, with which a releasable locking connection to the spreader arm can be made. For this purpose, the spreader arm preferably has pre-determined locking positions so that defined placement of the retaining elements along the spreader arms is possible. Thus retaining elements can be placed, in particular opposing one another on different spreader arms, precisely aligned to one another.

BRIEF DESCRIPTION OF THE DRAWINGS

This and other advantages of the invention will now be described in greater detail based on the drawings, in which.

DETAILED DESCRIPTION

Figure 1:
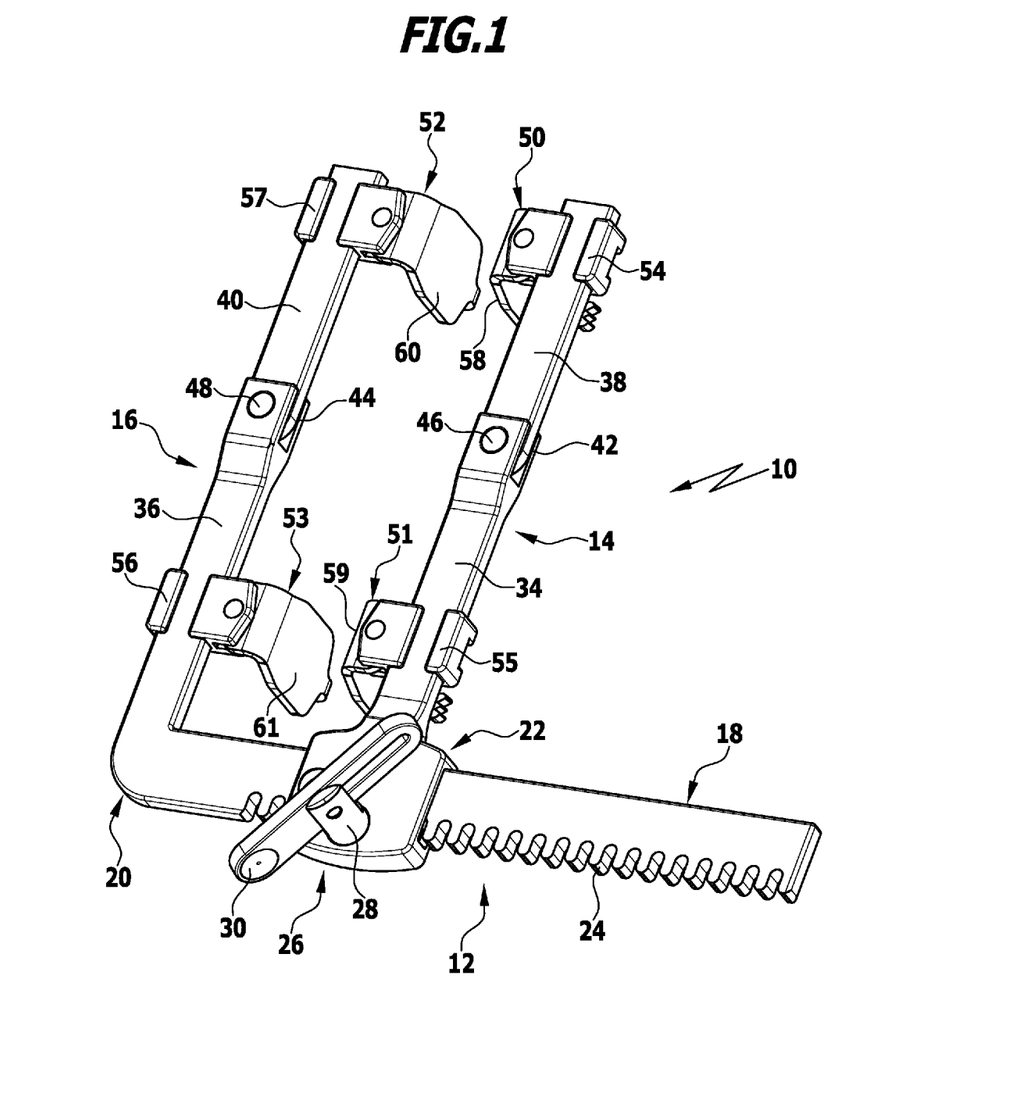
FIG. 1 shows an embodiment of a retractor according to the invention.

FIG. 1 shows an embodiment of a retractor 10 according to the invention, having a holding device 12 and two spreader arms 14 and 16 arranged on the holding device 12 and positionable at a variable spacing from one another. The two spreader arms 14 and 16 are arranged substantially perpendicularly to the longitudinal direction of the holding device 12 and parallel to one another and define the spreading plane of the retractor 10.

The holding device 12 comprises a substantially straight rail 18 on one end 20 of which one end of the second spreader arm 16 is formed integrally. The spreader arm 14 is arranged to be displaceable in the longitudinal direction of the rail 18. For this purpose, the spreader arm 14 has a bearing element 22 which engages round the rail 18 of the holding device 12.

The rail 18 has a substantially rectangular cross-section in which a row of teeth 24 is provided at a narrow side thereof. The bearing element 22 has a drive mechanism 26 with a rotary body (not shown in detail), for example, a pinion or a gearwheel, which meshes with the row of teeth 24. This rotary body is held rotationally fixed on a bearing shaft 28 which extends perpendicularly to the longitudinal axis of the rail 18 and to the spreading plane and is rotatably held in the bearing element 22. At the free end, oriented upwardly in the Figure, the bearing shaft 28 has a grip element 30 with which the rotary body can be rotated and, consequently, the spacing of the two spreader arms 14 and 16 from one another along the rail 18 can be changed.

The spreader arms 14, 16 each have straight first sections 34, 36 which are arranged adjacent to the holding device 12, and straight second sections 38, 40 which are pivotably held at the free end of the first sections 34, 36 of the spreader arms 14 and 16. The length of the first sections 34, 36 is somewhat greater than the length of the second sections 38, 40.

For the mounting of the second sections 38, 40, the first sections 34, 36 of the spreader arms 14 and 16 comprise forked bearing elements 42, 44 in each of which a holding device-side end of the second sections 38, 40 is held so as to be pivotable in the spreading plane by means of a pivot bearing 46 or 48.

Two retaining elements 50, 51 and 52, 53 are held on each of the spreader arms 14, 16. Each of the retaining elements 50 and 52 is arranged on a first section 34 and 36 and each of the retaining elements 51 and 53 is arranged on a second section 38 and 40 of the spreader arms 14 and 16. The retaining elements 50, 51, 52, 53 are each formed in two parts with a bearing part 54, 55, 56, 57 and retaining surfaces 58, 59, 60, 61 held thereon rotatable about an axis perpendicular to the spreading plane. The bearing parts 54, 55, 56, 57 are preferably configured such that they are held displaceably on their respective associated sections of the spreader arms 14 and 16 and can be fixed in different positions. Due to the somewhat greater length of the first sections 34, 36 in relation to the length of the second sections 38, 40, it is ensured that the retaining elements can be positioned symmetrically to the pivot bearings 46, 48 making use of the overall length of the second sections 38, 40.

Due to the division of each of the spreader arms 14 and 16 into two sections 34, 38 and 36, 40 and the pivotable mounting of the second sections on the first sections, mounting of the retaining elements 58, 59, 60, 61 with changeable positions in the spreading plane is achieved. During retraction of the longitudinally parted sternum of a patient, the substantial forces to be applied can be introduced differently regulated over the length of the parted sternum so that a gentler opening of the parted sternum is possible.

The pivotable mounting of the second sections 38, 40 on the first sections 34, 36 of the spreader arms 14, 16 can be realised in various ways.

Firstly, the second sections 38, 40 can be held resiliently on the first sections 34, 36 in a straight orientation, as shown in FIG. 1. This can be achieved, for example, by means of extension springs, compression springs or torsion springs, wherein the spring moduli for the individual second sections can be different and, in particular, adjustable. Only when the retraction forces occur due to the actuation of the drive mechanism 26 of the bearing element 22 do the second sections 38, 40 pivot in the spreading plane against the spring force of the mounting. The angles through which the second sections can be deflected from the straight line configuration are preferably limited by a stop. Preferably the stops limit the deflection to approximately 30°.

Furthermore, the pivot bearings 46, 48 can be replaced by pivot drives with which a deflection drive can be predetermined.

A device for locking the second sections in a pivot position, once reached, can also be provided.

The length of the first sections 34, 36 is greater than half the overall longitudinal extent of the spreader arms 14 and 16, so that the pivot bearings 46, 48 are arranged approximately in the centre of the longitudinal extent of the spreader arms 14, 16.

Figure 2:
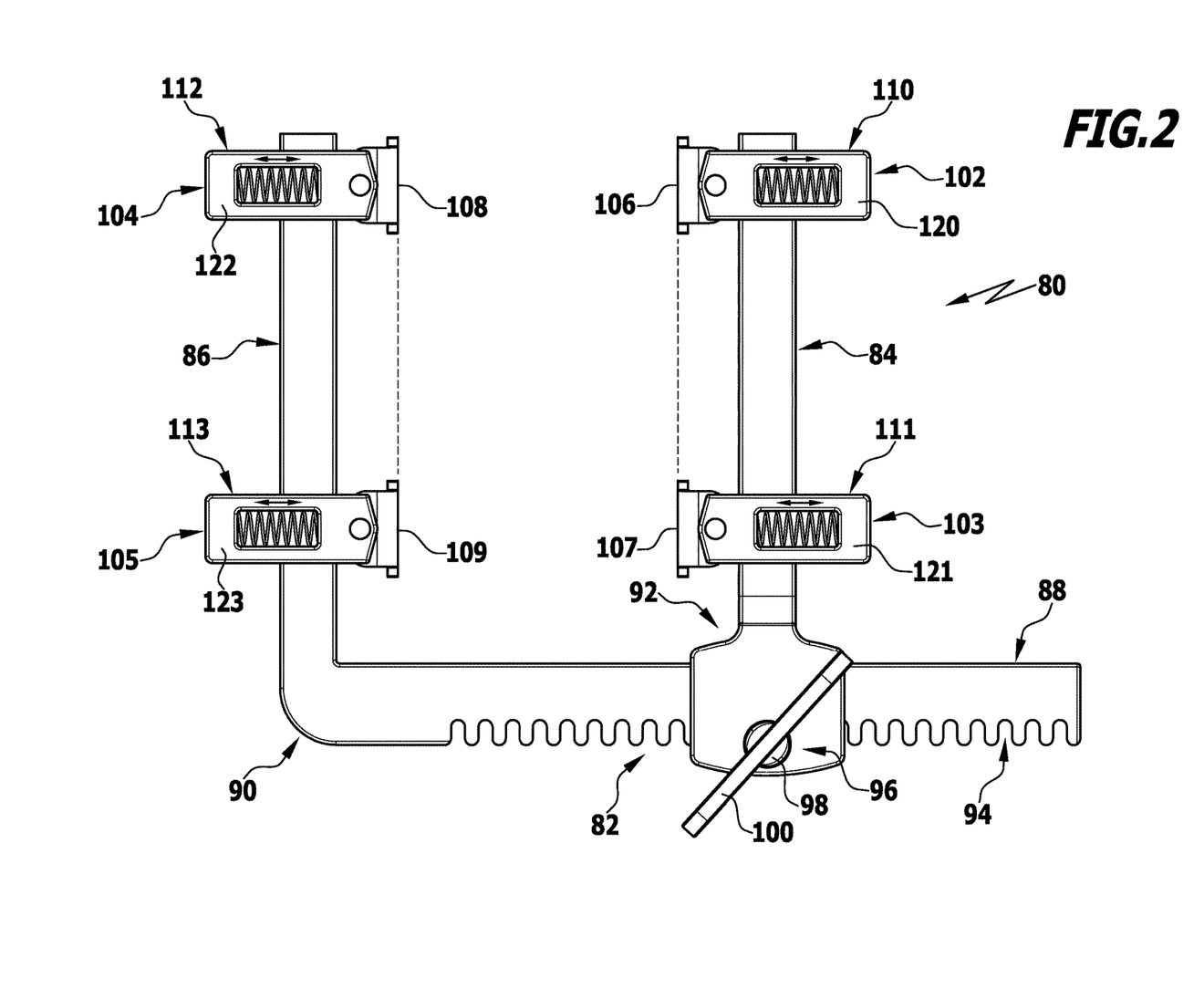
FIG. 2 shows another embodiment of a retractor according to the invention.

A further embodiment of the retractor according to the invention 80 is shown in FIG. 2. The retractor 80 comprises a holding device 82 and two straight, rigid spreader arms 84, 86 arranged parallel, of which the first spreader arm 84 is held at one side and is longitudinally displaceable on the holding device 82 or the rail 88 thereof, whilst the second spreader arm 86 is formed integrally and at right angles onto one end 90 of the holding device 82. The two spreader arms 84 and 86 define the spreading plane of the retractor 80.

The rail 88 is provided over the major part of its longitudinal extent and on a narrow side of its rectangular cross-section with a row of teeth 94.

The spreader arm 84 is arranged to be displaceable on the rail 88 with a bearing element 92. The bearing element 92 includes a drive mechanism 96 which comprises a rotary body (not shown in detail) which comprises, for example, a gearwheel which engages in the row of teeth 84. The drive mechanism 96 comprises a shaft 98 held in the bearing element 92, said shaft being rotatable by means of a grip element 100 so that a linear displacement of the spreader arm 84 along the longitudinal direction of the holding device 82 or along the rail 88 thereof results therefrom and therefore a change in the spacing between the two spreader arms 84 and 86.

Retaining elements 102, 103 and 104, 105 are arranged in pairs on the two rigid spreader arms 84, 86. The retaining elements 102, 103, 104, 105 are mounted on the spreader arms 84 and 86 preferably so as to be displaceable along the longitudinal direction of said spreader arms and are also preferably fixable at respective pre-defined positions.

Further preferably, the number of retaining elements provided corresponds to the number of ribs held on the sternum.

The retaining elements 102, 103, 104, 105 are also formed in a plurality of parts and comprise a holder part 110, 111, 112, 113 on which retaining surfaces 106, 107, 108, 109 are pivotably held, preferably about an axis perpendicular to the spreading plane. The holder parts 110, 111, 112, 113 comprise a bearing part (not shown in detail) which engages round the substantially rectangular cross-section of the spreader arms 84 or 86, and a resiliently biased holder 120, 121, 122, 123 thereon. The resilient biasing of the holders 120, 121, 122, 123 is preferably selected for the individual retaining elements 106, 107, 108, 109 depending on the position thereof, so that force can be applied to each region of the sternum during retraction according to the anatomical conditions.

Based on the resilient holding of the retaining elements 106, 107, 108, 109, the possibility exists of positionally adjustable mounting of the retaining elements or of the retaining surfaces which come into contact with the bone materials, so that the substantial forces that must be applied during retraction of a sternum can again be exerted in a regulated manner and adapted to the different elasticity of the sternum and the rib arches adjacent thereto.

Figure 3:
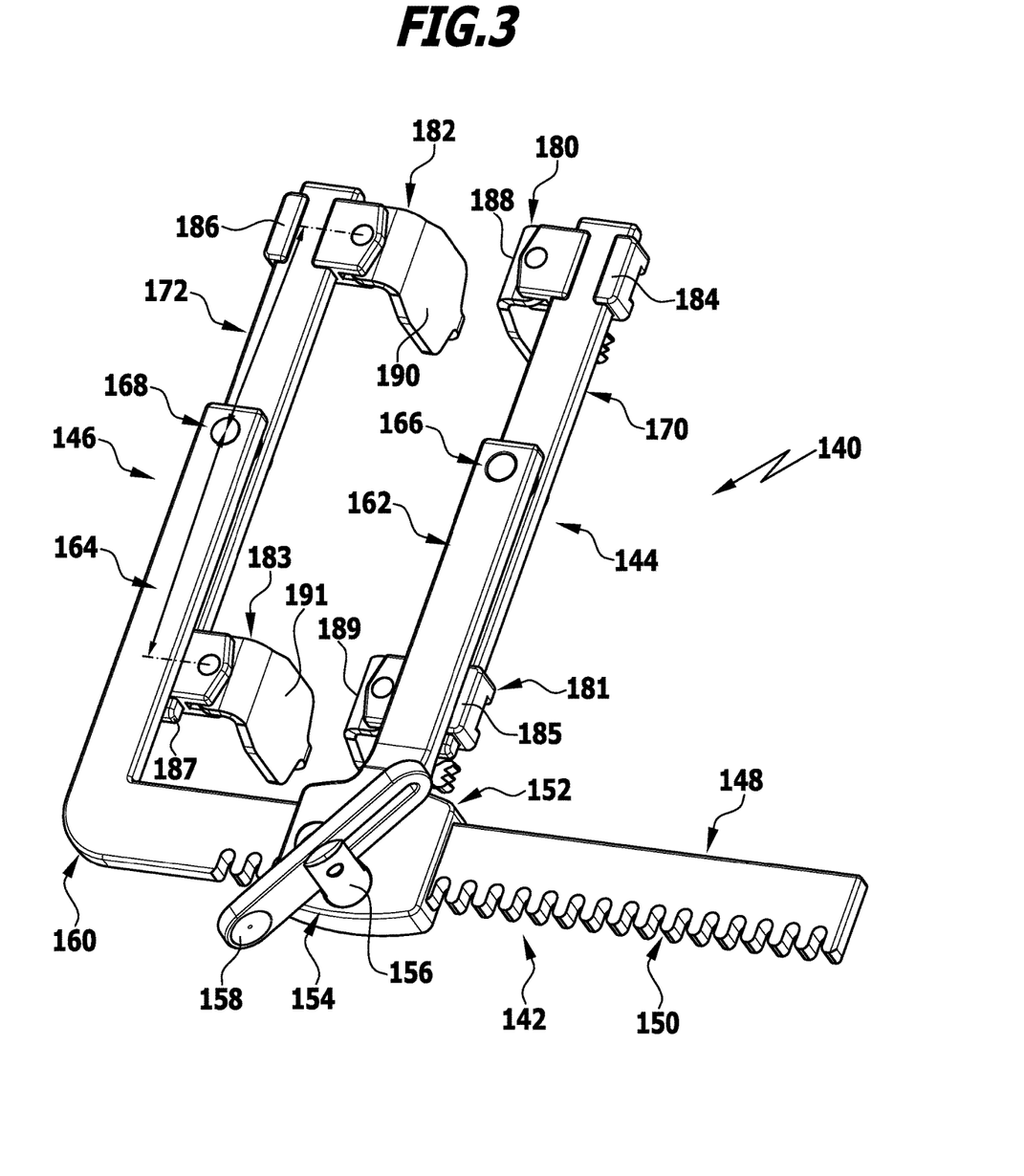
FIG. 3 shows another embodiment of a retractor according to the invention.

FIG. 3 shows a further embodiment of a retaining device 140 according to the invention with a holding device 142 and two spreader arms 144, 146 held on one side on the holding device 142. The holding device 142 comprises a rail 148 which is configured substantially straight and has a substantially rectangular cross-section. The rail 148 has a row of teeth 150 on one of its narrow sides.

The spreader arm 144 is displaceable along the longitudinal direction of the rail 148 so that the spreader arm 144 can be moved closer to the spreader arm 146 or the spacing of the two spreader arms from one another can be increased. For this purpose, the spreader arm 144 is displaceably held by means of a bearing element 152 on the holding device 142 or on the rail 148 thereof. The bearing element 152 comprises a drive mechanism 154 which comprises a rotary body (not shown in detail), for example, in the form of a pinion or a gearwheel which is mounted rotationally fixed on a drive shaft 156 which protrudes upwardly from the bearing element 152 and is equipped there with a grip element 158.

Through rotation of the shaft 156 with the aid of the grip element 158, by means of the rotation movement of the rotary body, a displacement of the spreader arm 144 along the rail 148 can take place. Preferably, the rotary body of the drive device 154 can be configured such that a self-blocking connection is formed between the rotary body and the row of teeth 150 of the rail 148.

The second spreader arm 146 is integrally formed onto one end 160 of the holding device 142. The two spreader arms 144, 146 lie in one plane, the spreading plane.

The two spreader arms 144, 146 are formed in two parts wherein a straight first section 162, 164 is held on the holding device 142 at a right angle. At their free end opposed to the holding device 142, the two first sections 162, 164 have bearing locations 166, 168 on each of which a straight second section 170, 172 of the spreader arms 144, 146 is pivotably held. Preferably, the second sections can be locked in an orientation parallel to the first sections, so that application of the retractor is simplified.

In a modified embodiment, only one spreader arm is formed in two parts, wherein a larger pivot angle of the second section of the divided spreader arm is to be permitted. During the retraction process, the position of the holding device is then changed. This embodiment has the advantage that the number of parts needed is reduced.

In contrast to the embodiment of FIG. 1, the second sections 170, 172 are not attached at one of the ends thereof to the first section 162, 164, but are centrally rotatable about an axis perpendicular to the spreading plane at the free end of the first sections 162, 164 of the spreader arms 144, 146. As a consequence, the second section 170, 172 overlaps with approximately half of the length thereof with the free end of the first sections 162, 164 of the spreader arms 144, 146.

The retractor 140 also has four retaining elements 180, 181, 182, 183 which, however, are held in pairs on the second sections 170, 172. Preferably, the retaining elements 180, 181, 182, 183 are held longitudinally displaceable on the second sections 170 and 172 and fixable in the respective pre-determined positions thereof.

The retaining elements 180, 181, 182, 183 are also formed, similarly to the retaining elements of the embodiment of FIG. 1, in two parts wherein a first part constitutes a holder part 184, 185, 186, 187 on which retaining surfaces 188, 189, 190, 191 are held pivotable about an axis perpendicular to the spreading plane.

When the retraction forces are applied to the longitudinally parted sternum, the second sections 170, 172 with their retaining elements 180, 181, 182, 183 automatically become oriented according to the resistance forces exerted by the bone material of the sternum and the rib arches adjacent thereto so that a positionally changeable mounting of the retaining elements is produced and a regulated introduction of forces according to the different elasticities of the individual sections of the parted sternum with the rib arches adjacent thereto is possible. This embodiment of the invention enables the matching of the forces without spring elements, resulting in advantages in relation to the non-linear spring moduli of the ribs in the sternotomy. In particular, this retractor according to the invention also reacts automatically and individually to different thoracic cages of the patients according to the leverage/force ratio.

Figure 4A:
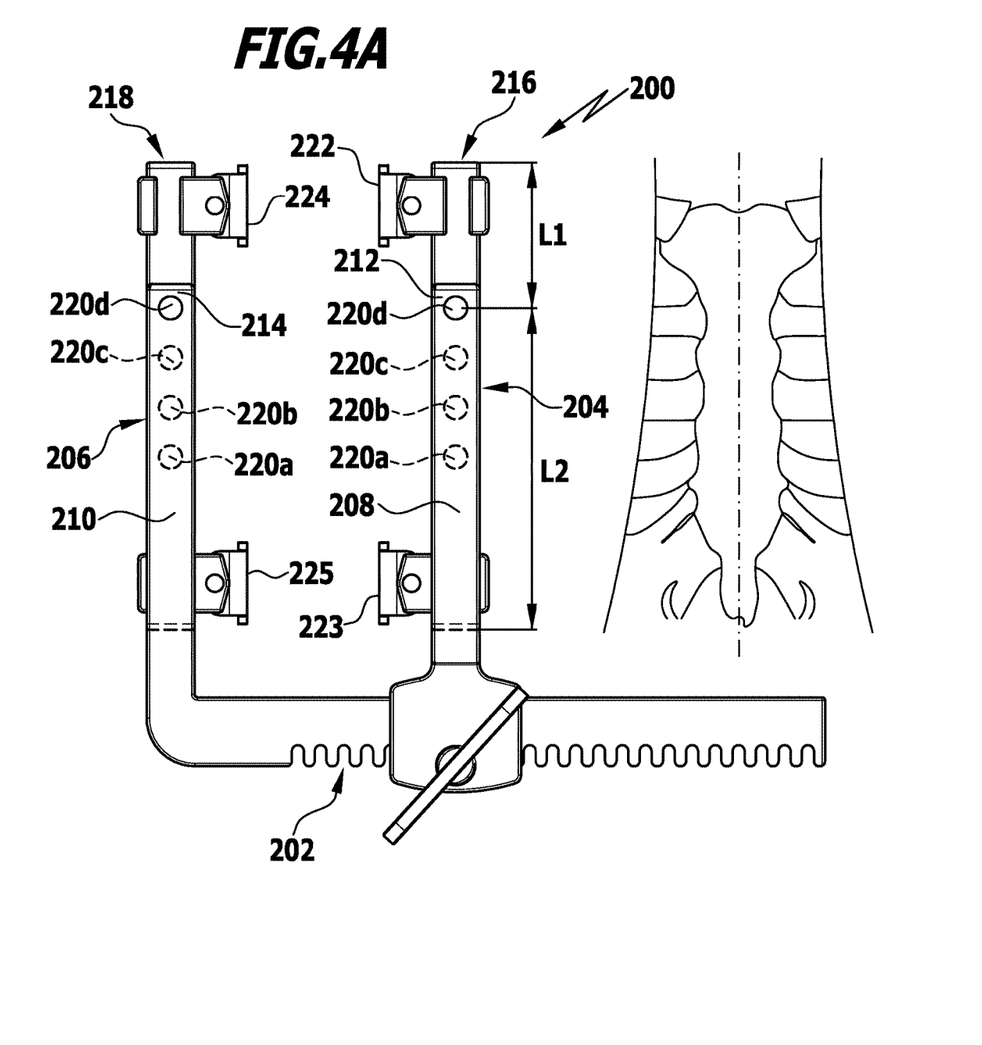
FIGS. 4A and 4B show a variant of the embodiment of the retractor of FIG. 3.
Figure 4B:
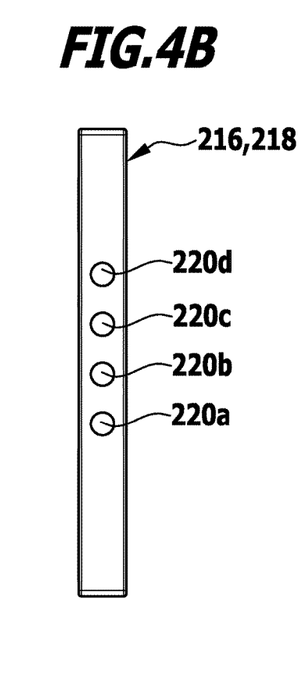

FIGS. 4A and 4B show a variant of the retractor 140 according to the invention of FIG. 3 in the form of a retractor 200. The retractor 200 comprises a holding device 202 and two spreader arms 204, 206 held thereon on one side and in one plane, the spreading plane.

The spreader arms 204, 206 are again formed in two parts and with a straight first section 208, 210, each held on the holding device 202 on one side. At their free end 212, 214 opposed to the holding device 202, they carry a straight second section 216, 218 which is pivotable about an axis perpendicular to the spreading plane. The second sections 216, 218 again overlap in large parts with the associated first section 208, 210 of the spreader arms 204, 206, so that both pairs are held on retaining elements 222, 223, 224, 225 on the respective second sections 216, 218 of the spreader arms 204, 206.

However, although in the embodiment of FIG. 3, the second sections are unchangeably pivotably centrally fixed on the associated first section, in the embodiment of FIGS. 4A and 4B, it is provided that the position of the mounting on the second section 216, 218 can be changed and preferably, for this purpose, a plurality of mounting locations 220a, 220b, 220c, 220d are provided on the second section 216, 218.

Thus the leverage of the sections L1 and L2 of the second sections 216, 218 of the spreader arms 204, 206 can be changed and therefore adapted according to the conditions for a patient, as shown schematically in FIG. 4.

Figure 5:
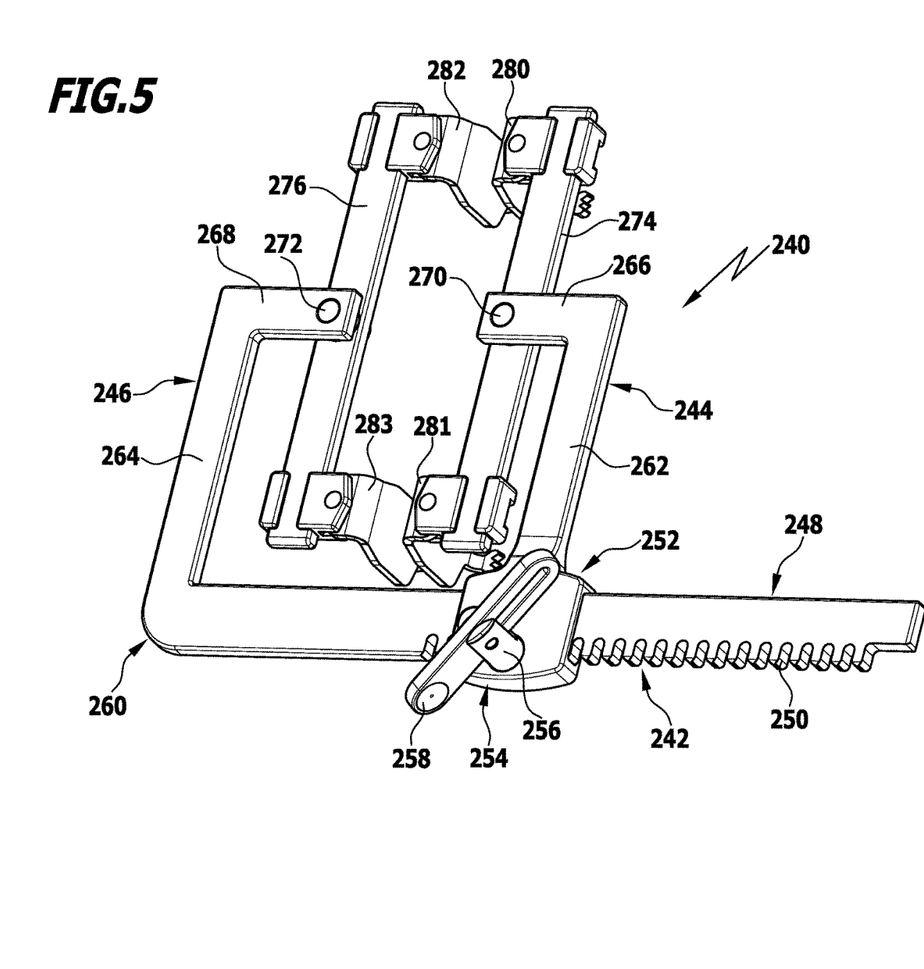
FIG. 5 shows a further variant of the embodiment of the retractor of FIG. 3.

FIG. 5 shows a further embodiment of the retaining device 240 according to the invention with a holding device 242 and two spreader arms 244, 246 held on one side of the holding device 242. The holding device 242 comprises a rail 248 which is formed substantially straight and has a substantially rectangular cross-section. The rail 248 has a row of teeth 250 on one of the narrow sides thereof.

The spreader arm 244 is displaceable along the longitudinal direction of the rail 248 so that the spreader arm 244 can be moved closer to the spreader arm 246 or the spacing of the two spreader arms from one another can be increased. For this purpose, the spreader arm 244 is displaceably held by means of a mounting element 252 on the holding device 242 or the rail 248 thereof. The bearing element 252 comprises a drive mechanism 254 which comprises a rotary body (not shown in detail), for example, in the form of a pinion or a gearwheel, which is mounted rotationally fixed on a drive shaft 256 which protrudes upwardly from the bearing element 252 and is equipped there with a grip part 258.

Through rotation of the grip part 258 and thereby of the drive shaft 256, by means of the rotation movement of the rotary body, a displacement of the spreader arm 244 along the rail 248 can take place. Preferably, the rotary body of the drive mechanism 254 can be configured such that a self-blocking connection is formed between the rotary body and the row of teeth 250 of the rail 248.

The second spreader arm 146 is integrally formed onto one end 260 of the holding device 242. The two spreader arms 244, 246 lie in one plane, the spreading plane.

The two spreader arms 244, 246 are formed in two parts wherein a first section 262 or 264 is held on the holding device 142 at a right angle. At their free end opposed to the holding device 242, the two first sections 262, 264 have angled regions 266, 268 projecting opposite one another, on which bearing locations 270, 272 are provided, on each of which a straight second section 274, 276 is pivotably held.

The retractor 240 has four retaining elements 280, 281, 282, 283 which are held, preferably displaceably, in pairs at the second sections 274, 276.

The retaining elements 280, 281, 282, 283 are configured similarly to the retaining elements 50, 51, 52, 53 of FIG. 1, so that reference can be made to the description of the retaining elements relating thereto.

When the retraction forces are applied to the longitudinally parted sternum, the two second sections 274, 276 become oriented according to the resistance forces exerted by the bone material of the sternum and the rib arches adjacent thereto so that, in this embodiment also, a positionally changeable mounting of the retaining elements is produced and a reglated introduction of forces takes place according to the different elasticities of the individual sections of the parted sternum with the rib arches adjacent thereto.

Figure 6:
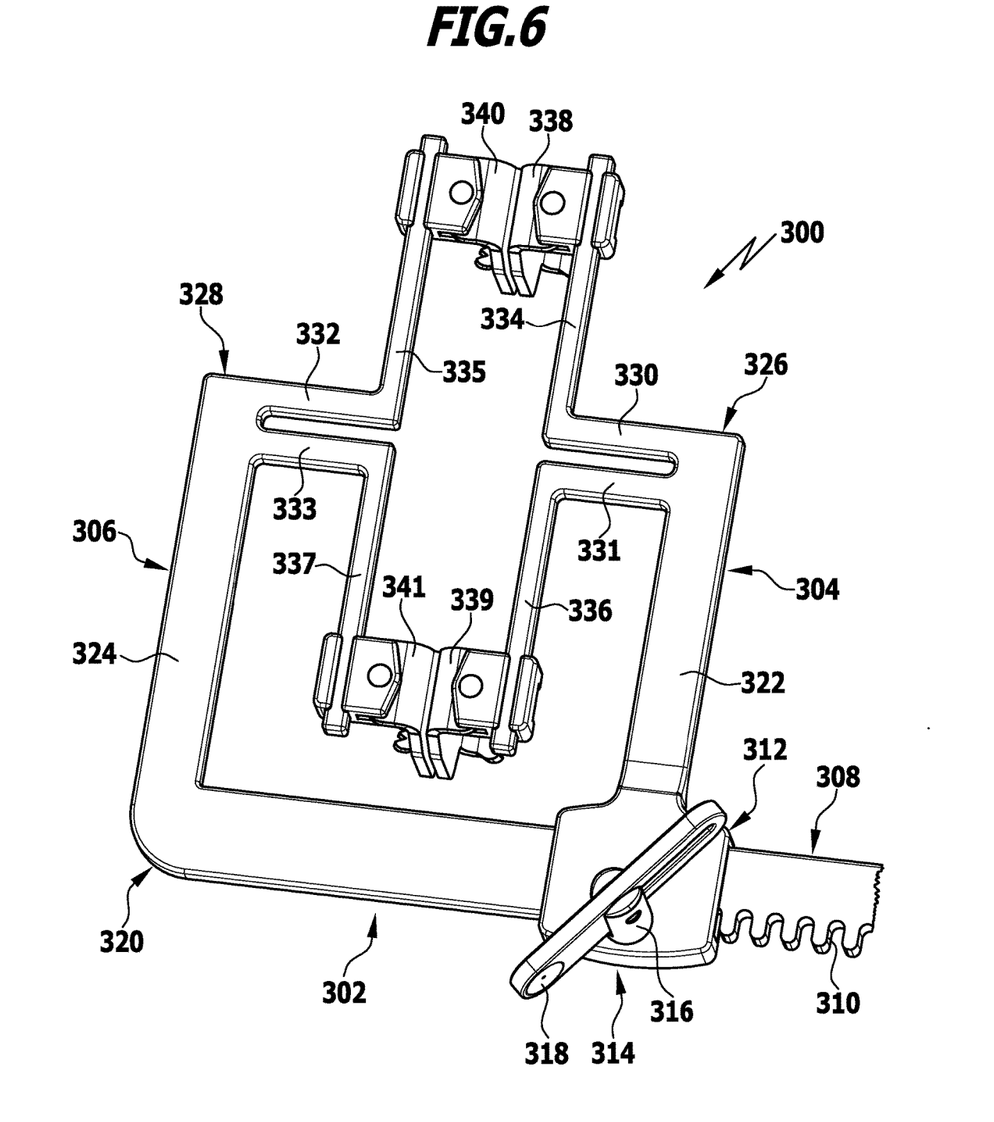
FIG. 6 shows another embodiment of a retractor according to the invention.

A further embodiment of a retractor of the present invention will now be described making reference to the retractor 300 illustrated in FIG. 6.

The retractor 300 comprises a holding device 302 and two spreader arms 304, 306 held at right angles on the holding device 302. The holding device 302 comprises a rail 308 which is formed substantially straight with a substantially rectangular cross-section and has a row of teeth 310 on one of the narrow sides thereof.

The spreader arm 304 is displaceable along the longitudinal direction of the rail 308 so that the spreader arm 304 can be moved closer to the spreader arm 306 or the spacing of the two spreader arms from one another can be increased. For this purpose, the spreader arm 304 is displaceably held on the rail 308 by means of a mounting element 312. The bearing element 312 comprises a drive mechanism 314 which comprises a rotary body (not shown in detail), for example, in the form of a pinion or a gearwheel which is mounted rotationally fixed on a drive shaft 316 which protrudes upwardly from the bearing element 312 and is equipped there with a grip element 318.

If the shaft 316 is rotated with the aid of the grip element 318, by means of the rotation movement of the rotary body which is mounted rotationally fixed on the drive shaft 316, a displacement of the spreader arm 304 along the rail 308 can take place. Preferably, the rotary body of the drive device 314 is configured such that a self-blocking connection is formed between the rotary body and the row of teeth 310 of the rail 308.

The second spreader arm 306 is formed integrally onto one end 320 of the holding device 302. The two spreader arms 304, 306 lie in one plane and thus define the spreading plane.

The two spreader arms 304, 306 are formed in a plurality of parts, wherein a first section 322, 324 is held on the holding device 302 at a right angle to the rail 308. At their ends remote from the holding device 302, the spreader arms 304, 306 have mutually opposed angled regions 326, 328 lying in the spreading plane and which are divided in forked manner in the spreading plane.

Preferably, the angled regions 326, 328 consist substantially of the fork prongs 330, 331 and 332, 333 which are arranged parallel.

Formed approximately at right angles onto the free ends of the parallel fork prongs 330, 331, 332, 333 are straight rail elements 334, 335, 336, 337 which, in pairs, assume the function of a second section of the spreader arms 304, 306.

The cross-section of the fork prongs 330, 331, 332, 333 and/or of the rail elements 334, 335, 336, 337 is selected so that sufficient elastic positional variability is obtained for the free ends of the rail elements 334, 335, 336, 337, which ensures that the retaining elements 338, 339, 340, 341 arranged thereon can exert forces which are adapted to the prevailing resistance forces during retraction of the parted sternum with the adjacent ribs. In each of these variants, the rail elements are held pivotably independently of one another in the spreading plane. The rail elements 334, 335, 336, 337 can also have different lengths.

It can also be advantageous if the flexural strength of the rail elements changes along the longitudinal direction in order thereby to realise, at each spacing of the fork prongs 330, 331, 332, 333, an elastic stiffness which is adapted to the ribs.

Furthermore, it can be provided in one variant that a stop delimits the maximum deflection of a rail element in the spreading plane.

Preferably, the retaining elements 338, 339, 340, 341 are arranged to be displaceable in the longitudinal direction of the rail elements 334, 335, 336, 337. By this means, the retractor according to the invention can also be adapted to the conditions of an current operation situation.

The retaining elements 338, 339, 340, 341 are substantially configured similarly to the retaining elements 50, 51, 52, 53 described above in relation to FIG. 1, so that reference can be made to the detailed description given there.

Figure 7:
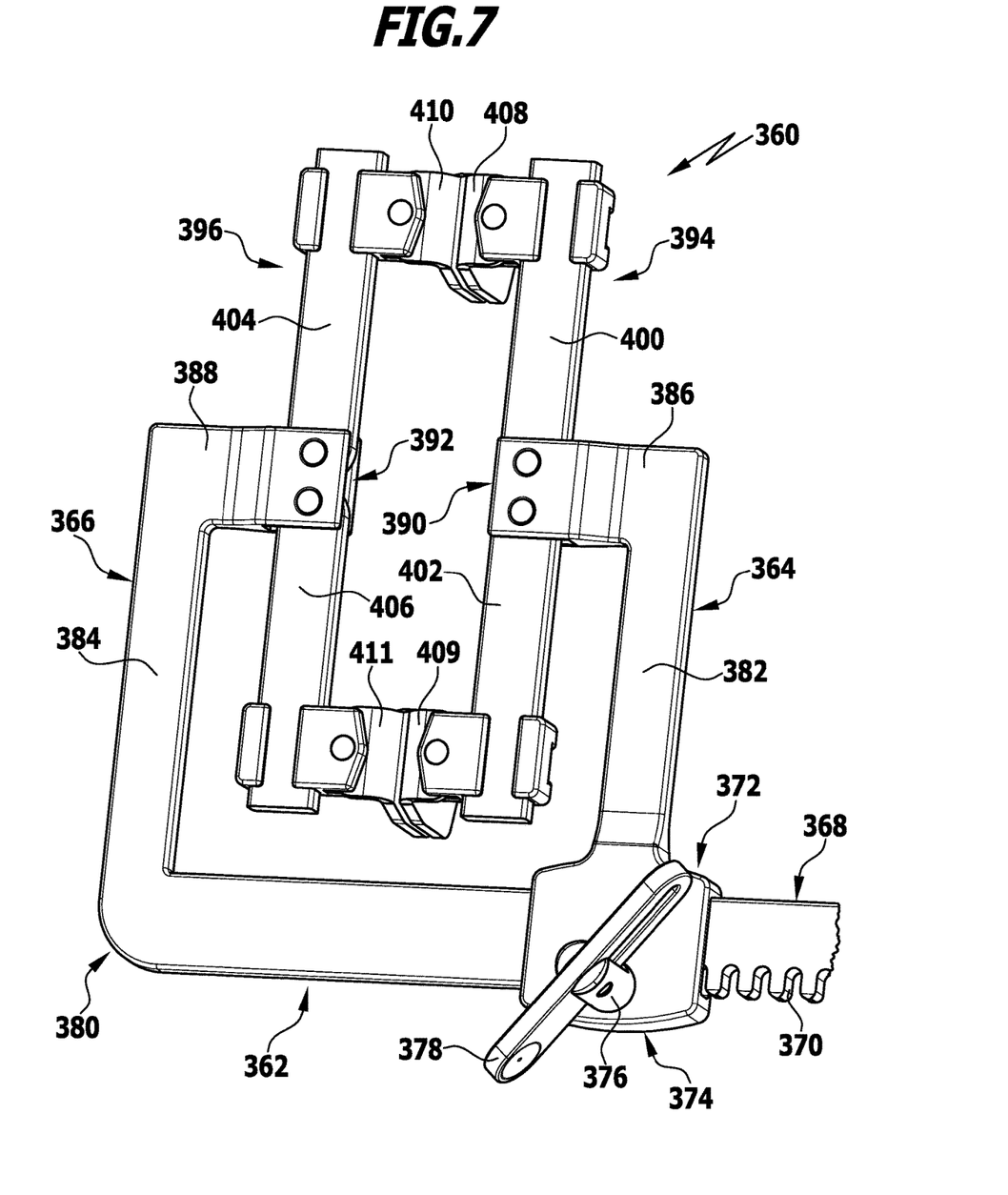
FIG. 7 shows another embodiment of a retractor according to the invention.

FIG. 7 shows a further embodiment of the retractor 360 according to the invention with a holding device 362 on one side of which two spreader arms 364, 366 are held. The holding device 362 comprises a rail 368 which is formed substantially straight with a substantially rectangular cross-section, on one of the narrow sides of which a row of teeth 370 is formed.

The spreader arm 364 is displaceable along the longitudinal direction of the rail 368 so that the spreader arm 364 can be moved closer to the other spreader arm 366 or away from the other spreader arm 366. The two spreader arms 364, 366 are oriented parallel to one another and define the spreading plane of the retractor 360 according to the invention.

The spreader arm 364 is displaceably held with a holding device 372 on the rail 368 by means of a bearing element 372, wherein the bearing element 372 comprises a drive mechanism 374 which comprises a rotary body (not shown in detail), for example, in the form of a pinion or a gearwheel which is mounted rotationally fixed on a drive shaft 376. The drive shaft 376 protrudes upwardly out of the bearing element 372 and is equipped at the free end thereof with a grip part 378.

With the aid of the grip element 378, the drive shaft 376, and therewith the rotary body, can be rotated so that, resulting therefrom, the bearing element 372 and the spreader arm 364 held thereon can be moved in the longitudinal direction of the rail 368. Preferably, the rotary body of the drive device 374 can be configured such that a self-blocking connection is formed between the rotary body and the row of teeth 370 of the rail 368. The spreader arm 366 is formed with one end thereof onto one end 380 of the holding device 362.

The two spreader arms 364, 366 are formed in two parts, wherein a first section 382, 384 is held on the holding device 362 at a right angle. At their free end opposed to the holding device 362, the two first sections 382, 384 have angled regions 386, 388, which are also arranged in the spreading plane of the retractor 360. Bearing locations 390, 392 are provided at the free ends of the angled regions 386, 388.

The second sections 394, 396 of the spreader arms 364, 366 are configured as paired rail elements 400, 402 and 404, 406, which are respectively held with one end thereof pivotable at the bearing locations 390, 392. The mounting of the rail elements is achieved preferably in resilient manner, in particular by means of extension springs, compression springs or torsion springs (not shown), wherein the spring constants of the individual rail elements can be differently selected. Due to the sprung mounting, the rail elements 400, 402, 404, 406 are held in a substantially parallel orientation to the first spreader arm section 382, 384 before the retraction movement starts.

The rail elements 400, 402, 404, 406 can also have different lengths.

The rail elements 400, 402, 404, 406 carry, at the free ends thereof, retaining elements 408, 409, 410, 411, which are configured similarly to the retaining elements 50, 51, 52, 53 described above in relation to FIG. 1, so that reference can be made to the detailed description of the retaining elements given there.

Preferably, the retaining elements 408, 409, 410, 411 are arranged along the longitudinal direction of the straight rail elements 400, 402, 404, 406 and thus permit positioning adapted to the respective application case.

Due to the elastically pivotable mounting of the rail elements 400, 402, 404, 406, during retraction of the spreader arms 364, 366, the retraction force is exerted adequately on the respective sections of the parted sternum and on the rib arches adjacent thereto.

Figure 8:
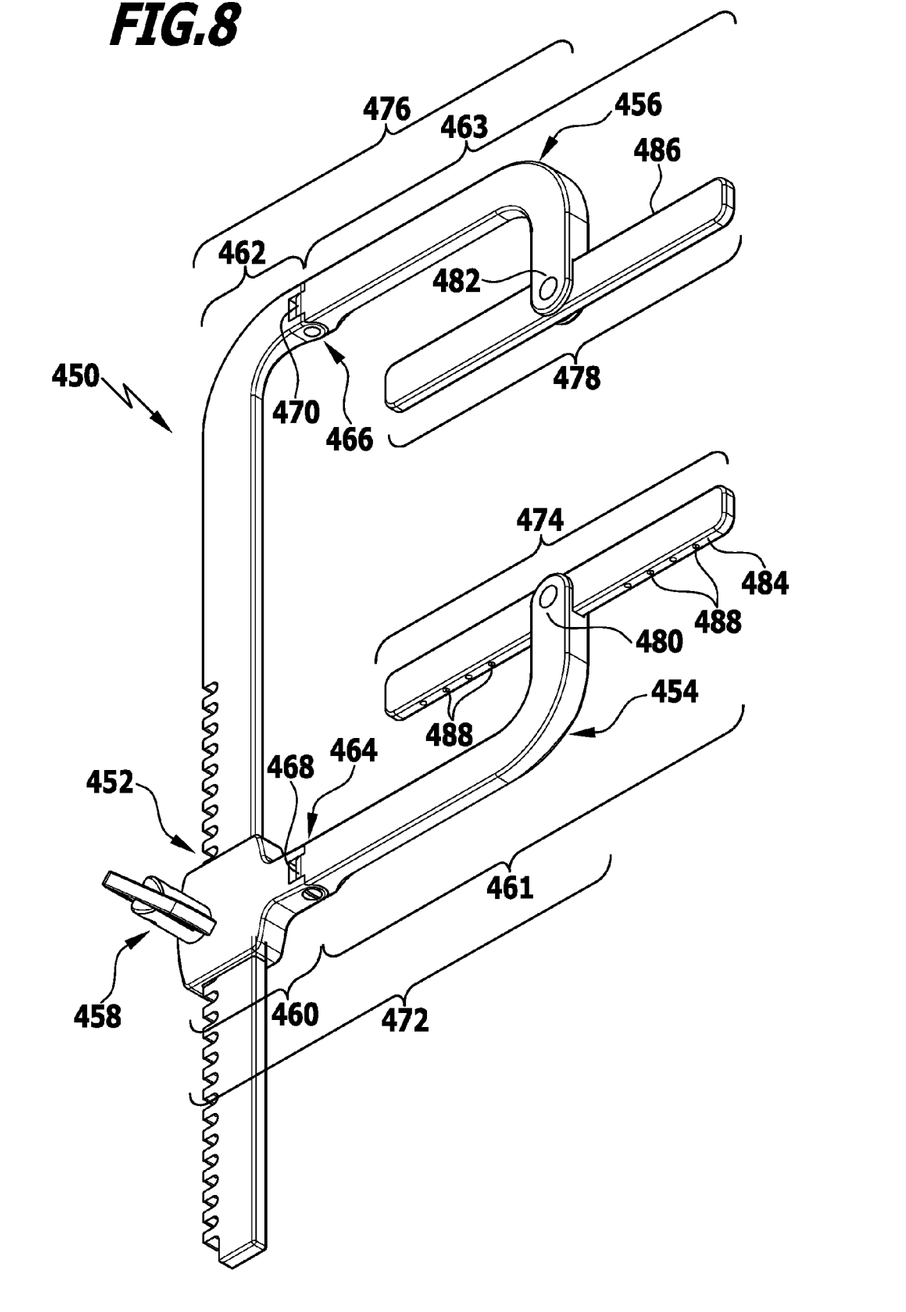
FIG. 8 shows another embodiment of a retractor according to the invention.

FIG. 8 shows a surgical retractor 450 in which the principles of the present invention are also applied.

Two spreader arms 454, 456 are held on a holding device 452, wherein the spreader arm 456 is formed integrally onto the holding device 452, whereas the spreader arm 454 is held on the holding device 452 displaceable by means of a drive mechanism 458.

The spreader arms 454 and 456 are each divided into two segments 460, 461 and 462, 463, of which the respective first segment 460 or 462 is held on the holding device 452 in a fixed, substantially unchangeable orientation to the spreading plane of the retractor 450.

The two segments 460, 461 and 462, 463 are pivotably connected to one another by means of a joint 464, 466 in each case, wherein the pivot angle of the second segments 461, 463 to the respective associated first segment 460, 462 is limited by means of a stop 468, 470 so that, for example, in the embodiment shown in FIG. 8, the second segments 461, 463 are pivotable only downwardly out of the orientation shown so that the holding device 452 which typically comes to lie laterally along the torso of the patient can be pivoted downwardly so that the space required by the retractor 450 seen in the spreading plane is minimised.

In the retractor of FIG. 8, another concept of the present invention is also realised, specifically the subdivision of the spreader arms 454, 456 into a first and a second section, of which the respective first section 472, 476 is held directly on the holding device 452 and on the respective free end 480 or 482 thereof holds the second section 474 or 478 pivotable in the spreading plane. The free ends 480, 482 of the first sections are each configured angled opposing one another in the spreading plane relative to the longitudinal direction of the spreader arms 454 or 456.

With regard to the subdivision into first and second sections of the spreader arms 454 and 456, the concept substantially corresponds to the concept shown in, and described in relation to, FIG. 5, so that for further details, reference can be made to the description of FIG. 5.

Furthermore, in the context of the embodiments of FIG. 8, it is provided that the retaining elements can be mounted at different defined positions along the second sections 474, 478 of the spreader arms. For this purpose, the second sections 474, 478 have recesses 488 as locking positions on the respective rear side 484, 486 thereof, into which retaining elements can be fixed in locking manner, as described below in relation to FIGS. 9A and 9B in detail.

Due to the configuration of the locking positions 488 on the second sections 474 and 478 of the two spreader arms 454, 456, it is possible by simple means to place retaining elements positioned opposing and oriented toward one another on the second sections 474, 478 of the two spreader arms.

During a retraction with the surgical retractor 454, adaptation of the forces exerted on the parted sternum again takes place automatically in that the second sections 474, 478 can be pivoted in the spreading plane according to the forces occurring and thus exert the retraction forces in an adapted manner on the parted sternum.

Figure 9A:
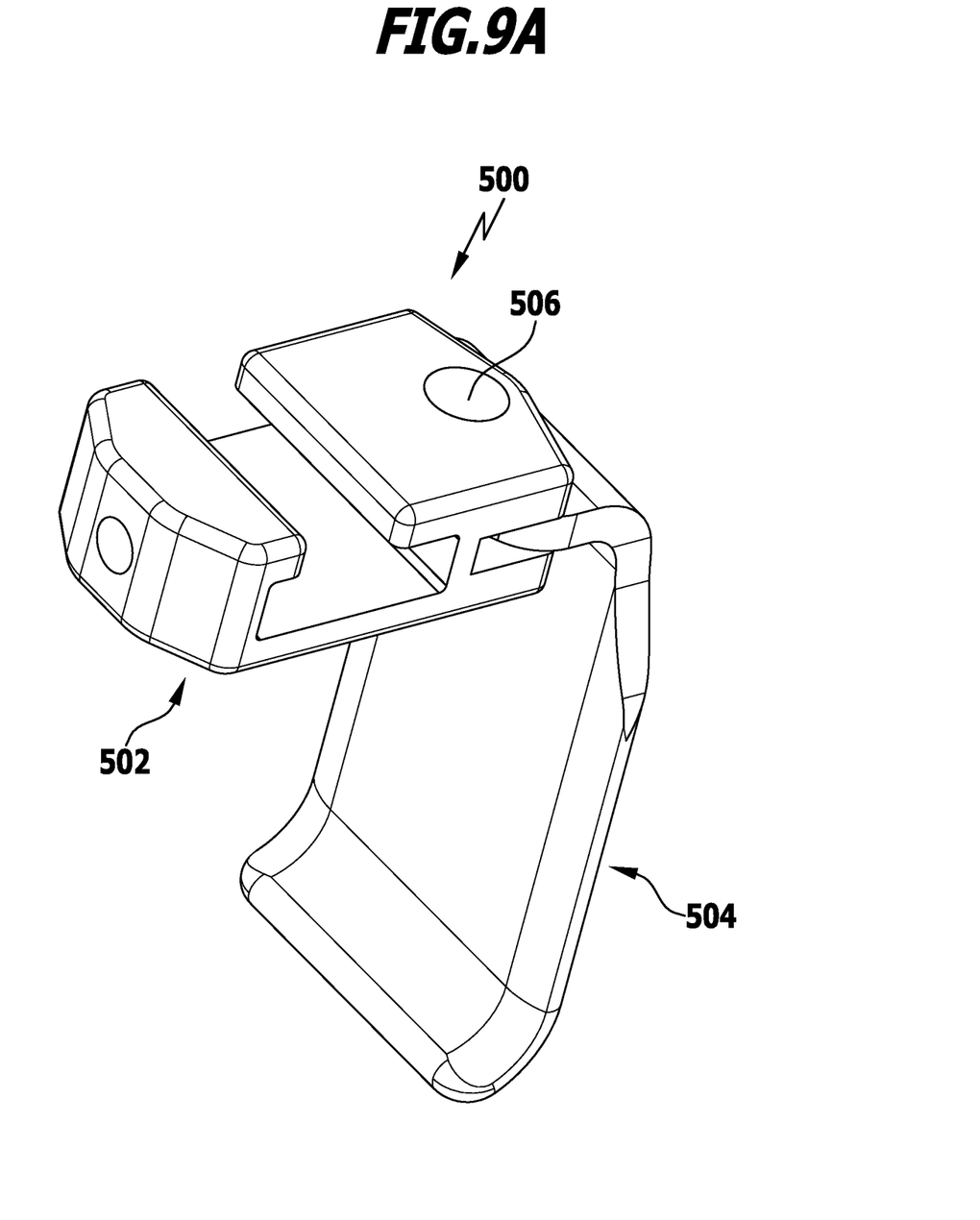
FIGS. 9A and 9B show a preferred retaining element for a retractor according to the invention.
Figure 9B:
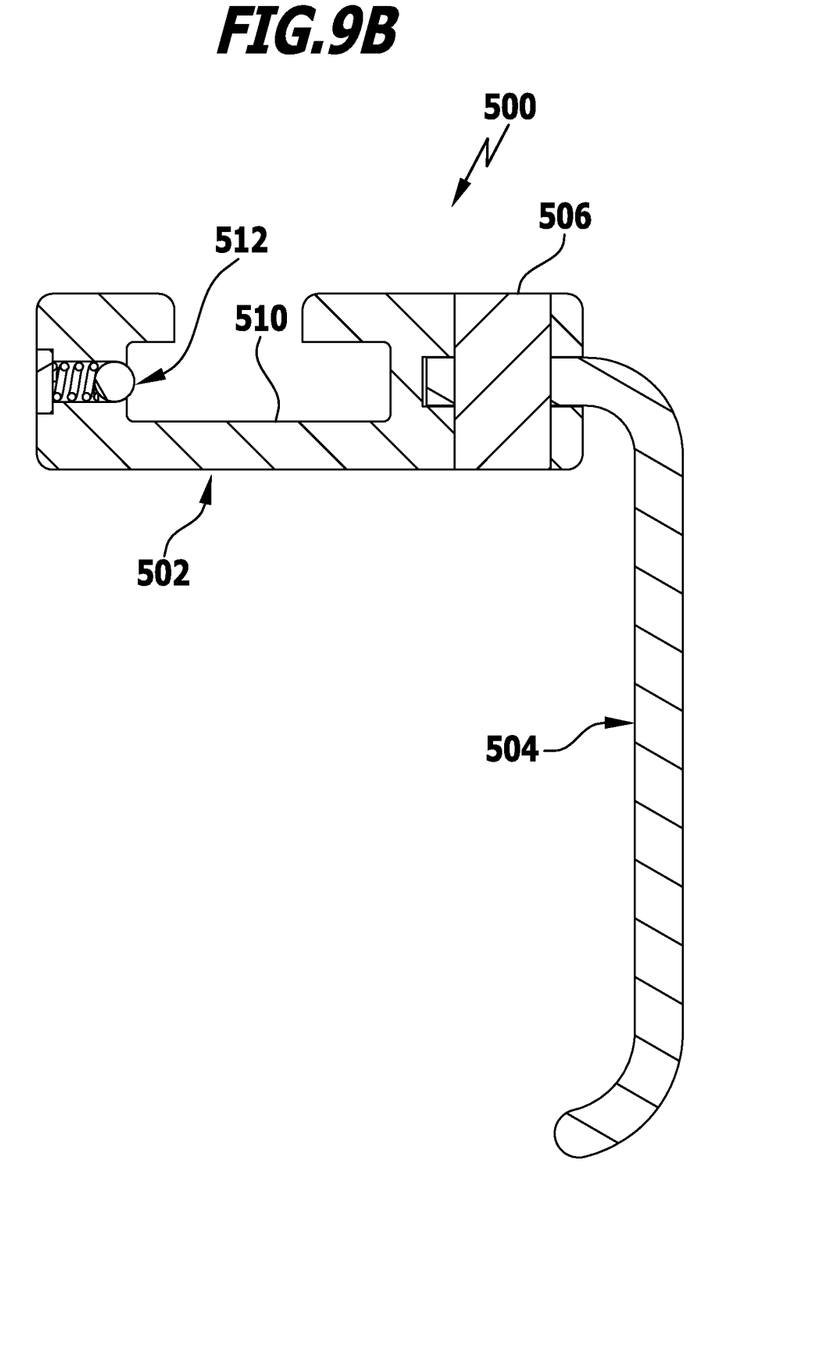

FIGS. 9A and 9B show a specific embodiment of a retaining element 500 which is configured in two parts and comprises a bearing element 502 and a retaining surface 504.

The retaining surface 504 is mounted on the bearing element 502, rotatable about an axis 506 perpendicular to the spreading plane.

The bearing element 502 has a substantially rectangular cross-section on which on one side, the retaining surface 504 is arranged with the rotation axis 506.

Provided in the rectangular cross-section of the bearing element 502 is a rectangular recess 510 which substantially corresponds, in the cross-section thereof, to the cross-section of the second section 474 or 478 of the retractor 450.

The recess 510 accommodates the cross-section of the second sections 474, 478 of the spreader arms 454 or 456 in sliding manner and can be placed, due to a spring-loaded ball thrust member 512 arranged on the narrow side of the bearing part 502 opposed to the bearing 506, at the predefined locking positions 488 of the second sections 474 or 478.

What is claimed is:

1. Surgical retractor, particularly for the spreading of a parted sternum, comprising:
    a holding device,
    two spreader arms, said spreader arms each being held with one end on the holding device at a spacing from one another that is adjustable in a retraction direction in a spreading plane, and
    at least two retaining elements arranged on each of the spreader arms,
    wherein:
    at least one of the retaining elements is mounted positionally adjustable in the retraction direction relative to an end of the spreader arm held on the holding device,
    both spreader arms are subdivided into two sections, a first section of each spreader arm held substantially rigidly on the holding device and a second section of the spreader arms held on the first section rotatable about a pivot axis perpendicular to the spreading plane,
    two retaining elements are arranged on the second section,
    the retaining elements are arranged on both sides of the pivot axis.

2. Surgical retractor according to claim 1, wherein the at least one retaining element is mounted in a position in the retraction direction resiliently relative to the spreader arm.

3. Surgical retractor according to claim 1, wherein the first section of a subdivided spreader arm has a length which is greater than half of an overall longitudinal extent of the spreader arm.

4. Surgical retractor according to claim 1, wherein the second section of the spreader arm is resiliently held in a starting position with a preferably coaxial orientation relative to the first section.

5. Surgical retractor according to claim 1, wherein the pivotability of the second section relative to the first section is limited by a stop.

6. Surgical retractor according to claim 1, wherein the second section is lockable in a position pivoted relative to the first section.

7. Surgical retractor according to claim 1, wherein the second section is pivotable relative to the first section by means of a drive.

8. Surgical retractor according to claim 7, wherein the drive is configured to be self-locking.

9. Surgical retractor according to claim 1, wherein the first section is configured to be substantially linear.

10. Surgical retractor according to claim 1, wherein:
    the first section, at an end thereof remote from the holding device, is configured to be angled in the spreading plane,
    an angled region of the first section is oriented in a direction toward the other spreader arm, and
    the pivot axis is arranged in the angled region of the first section.

11. Surgical retractor according to claim 10, wherein the second section is configured flexibly elastically deformable in the spreading plane.

12. Surgical retractor according to claim 10, wherein the second section is subdivided into two longitudinal elements which are arranged spaced apart from the first section in opposite directions.

13. Surgical retractor according to claim 1, wherein the pivot axis for the second section is formed by a bearing element which is displaceably held on the first section.

14. Surgical retractor according to claim 1, wherein the first section contains a flexibly elastic region and the second section is held on the flexibly elastic region of the first section.

15. Surgical retractor according to claim 1, wherein the retaining elements are arranged adjustably along a longitudinal direction of the spreader arm.

16. Surgical retractor according to claim 1, wherein the retaining elements are arranged offset relative to one another in a longitudinal direction of both spreader arms.

17. Surgical retractor according to claim 1, wherein:
    at least one of the retaining elements is configured in two parts,
    a first part of the at least one retaining element forms a bearing part and is held on the spreader arm and a second part of the at least one retaining element forms a retaining surface, which is mounted to be movable on the first part.

18. Surgical retractor according to claim 17, wherein the second part is held pivotable about an axis perpendicular to the spreading plane.

19. Surgical retractor according to claim 17, wherein the second part is held pivotable about an axis parallel to the spreading plane.

20. Surgical retractor according to claim 17, wherein:
- at least one of the retaining elements has a retaining surface which is subdivided into two sections,
- a first section is held on the spreader arm and a second section is mounted on the first section to be pivotable about an axis oriented parallel to a longitudinal direction of the spreader arm.

21. Surgical retractor according to claim 1, wherein:
- at least one of the retaining elements has a retaining surface which is subdivided into two sections,
- a first section is held on the spreader arm and a second section is held on the first section at a variable spacing from the spreading plane.

22. Surgical retractor according to claim 21, wherein the second section is pivotable about an axis which is parallel to a longitudinal direction of the spreader arm.

23. Surgical retractor according to claim 1, wherein at least one of the retaining elements has a retaining surface for the sternum which is configured bent over at a free end thereof.

24. Surgical retractor according to claim 1, wherein at least one of the retaining elements has a retaining surface for the sternum which is configured tapered at a free end thereof.

* * * * *